United States Patent
Berberich

[11] Patent Number: 5,959,457
[45] Date of Patent: Sep. 28, 1999

[54] CIRCUIT ARRANGEMENT FOR MEASURING THE RESISTANCE OF A RESISTANCE SENSOR

[75] Inventor: Reinhold Berberich, Frankfurt, Germany

[73] Assignee: VDO Adolf Schindling AG, Frankfurt, Germany

[21] Appl. No.: 08/887,035

[22] Filed: Jul. 2, 1997

Related U.S. Application Data

[63] Continuation of application No. 08/498,364, Jul. 5, 1995, abandoned.

[30] Foreign Application Priority Data

Jul. 14, 1994 [DE] Germany .............................. 44 24 833

[51] Int. Cl.⁶ .............................. G01R 27/02; G01R 29/02
[52] U.S. Cl. .......................... 324/710; 324/694; 324/689; 318/483
[58] Field of Search .............................. 318/483, DIG. 2; 324/710, 712, 445, 694, 689

[56] References Cited

U.S. PATENT DOCUMENTS

| | | | |
|---|---|---|---|
| 3,501,694 | 3/1970 | Ito | 324/709 |
| 3,766,471 | 10/1973 | Pullman | 324/709 |
| 4,467,272 | 8/1984 | Hassler | 324/607 |
| 4,609,882 | 9/1986 | Gehring | 324/327 |
| 4,703,237 | 10/1987 | Hochstein | 318/483 |
| 5,166,729 | 11/1992 | Rathbun | 324/445 |
| 5,455,513 | 10/1995 | Brown | 324/445 |

FOREIGN PATENT DOCUMENTS

| | | |
|---|---|---|
| 3540031 | 2/1987 | Germany . |
| 3812633 | 10/1989 | Germany . |
| 9008680 | 8/1990 | WIPO . |

*Primary Examiner*—Vinh P. Nguyen
*Assistant Examiner*—Jose M. Solis
*Attorney, Agent, or Firm*—Martin A. Farber

[57] ABSTRACT

In a circuit arrangement for measuring the resistance of a resistance sensor, for instance a wetness sensor, which is connected to an evaluation circuit, there is a galvanic separation, formed preferably by an isolating transformer, between the resistance sensor and the evaluation circuit.

17 Claims, 1 Drawing Sheet

CIRCUIT ARRANGEMENT FOR MEASURING THE RESISTANCE OF A RESISTANCE SENSOR

This application is a continuation of my co-pending, now abandoned application Ser. No. 08/498,364 filed Jul. 5, 1995.

FIELD AND BACKGROUND OF THE INVENTION

The present invention relates to a circuit arrangement for measuring the resistance of a resistance sensor, for instance a wetness sensor, which is connected to an evaluation circuit.

By way of two example, sensor resistors in the form of strip-shaped electrodes which are interlaced in one another are used for measuring the wetness of the windshield of a motor vehicle. If drops of water contact the two electrodes, then the resistance decreases. The decrease in resistance can be used for automatically controlling a windshield wiper. For a measurement of the resistance, it is necessary fundamentally to apply a voltage to the resistance sensor. However, dc portions of the voltage to be applied can produce electrolysis phenomena between the electrodes, which phenomena leads finally to a limiting of the life of the resistance sensors. A device for controlling a drive means for a vehicle accessory having such a sensor is described, for instance, in WO 90/08680.

SUMMARY OF THE INVENTION

The object of the present invention is to prevent electrolysis phenomena on resistance sensors, particularly wetness sensors.

This object is achieved with the circuit arrangement of the invention, in the manner that a galvanic separation is present between the resistance sensor and the evaluation circuit. It is preferable for the galvanic separation to be provided by an isolating transformer.

The circuit arrangement of the invention has the advantage of a galvanic separation between the sensor itself and the evaluation circuit. Thus, no direct voltage acts on the sensor. Thereby, electrolytic deposits on so that electrolytic deposits on or removals from the electrodes of the sensor, or which may break off from the electrodes, are prevented. Although wetness sensors can be operated in a particularly advantageous manner as a result of the circuit arrangement of the invention, the circuit arrangement of the invention is also suitable for use with other resistance sensors, i.e. with sensors in which the resistance of a sensor element is dependent on a physical value which is to be measured.

In order to avoid lead-throughs for the wires in the window of the vehicle, the circuit arrangement of the invention can further be developed in the manner that the resistance sensor and the evaluation circuit are connected inductively through the window of the vehicle.

One advantageous development of the circuit arrangement of the invention is that the resistance sensor is connected to a first winding of an isolating transformer. A second winding of the isolating transformer is acted on by a pulse-like voltage in the manner that, during in each case of one pulse, there is a rise in the current through the second winding. Furthermore means are and in means being provided for measuring the length of time which passes between the start of the pulse and the current reaching a predetermined threshold in the second winding.

A further development of this embodiment provides that this second winding is connected, in series with a measurement resistor, to one pole of a source of operating voltage and, via a switching transistor, to the other pole of the source of operating voltage. Also, the junction of the second winding with the measurement resistor is connected to the one input of a difference amplifier the other input of which can be acted on by a predetermined potential.

In the case of this further development, it can be provided that the switching transistor can be controlled by a microcomputer and that the output of the difference amplifier is connected to an input of the microcomputer. This is particularly advantageous when the microcomputer, on the basis of the specific requirements present, is to control the measuring process and, in this connection, determines the period of time by a counting process.

With the aforementioned development it may, however, also be advantageous for the output of the difference amplifier to be connected furthermore, via a resistor, to the non-inverting input of the difference amplifier and, via an inverter, to the control input of the switching transistor, and for the output of the difference amplifier to be connected with an input of a microcomputer. In this case, the circuit arrangement of the invention is designed to be self-excited so that the microcomputer is programmed for measuring the frequency. Should this frequency be too high for the computer or because of other programs which are also to be run by the microcomputer, then, in accordance with a further development, the input of the microcomputer can be connected via a frequency divider to the output of the difference amplifier.

In order to avoid high negative voltage peaks upon the disconnecting of the current, it is provided, in accordance with another further development of the circuit arrangement of the invention, that a diode is connected in parallel to the second winding and the measurement resistor.

BRIEF DESCRIPTION OF THE DRAWINGS

With the above and other objects and other advantages in view, the present invention will become more clearly understood in connection with the detailed description of a preferred embodiment, when considered with the accompanying drawings of which.

Identical parts are provided with identical reference numerals in the figures.

DETAILED DESCRIPTION OF THE PREFERRED EMBODIMENT

Figure 1:
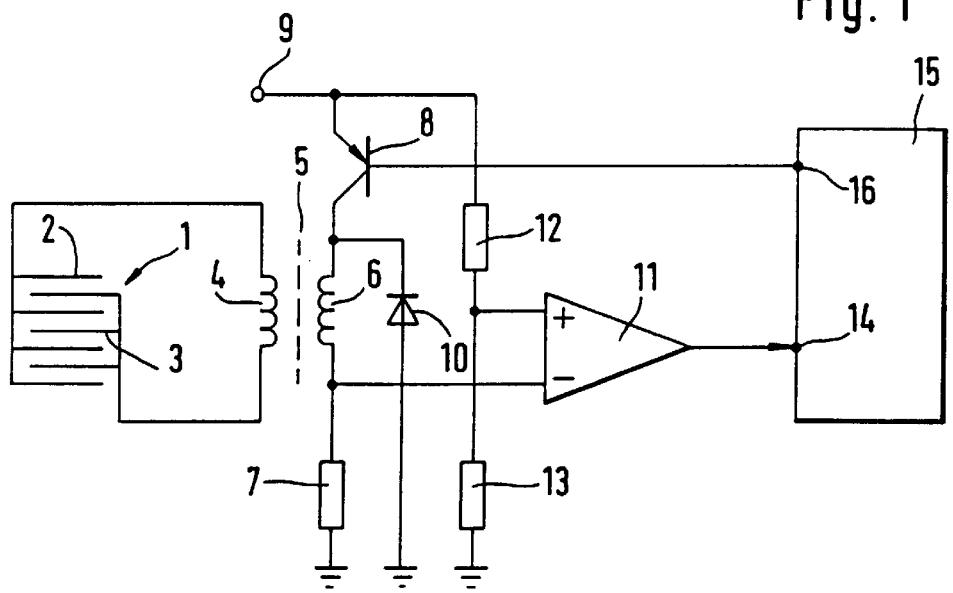
FIG. 1 shows a first embodiment.

The wetness sensor 1 consists of electrodes 2, 3 of conductive material which are applied on the windshield (not shownin FIG. 1–3 ) of a motor vehicle. As soon as drops of rain fall on the windshield, the resistance between the electrodes 2, 3 is reduced, which is noted by means of the circuit arrangement of the invention. The electrodes 2, 3 of the wetness sensor are connected to the ends of a first winding 4 of an isolating transformer 5.

The second winding 6 is connected in series with a measurement resistor 7 and the collector-emitter path of a switching transistor 8 between ground potential and the positive pole 9 of a source of operating voltage which is otherwise not shown. In parallel to the second winding 6 and the measurement resistor 7, there is a diode 10 which, after the disconnecting of the switching transistor 8, briefly takes over the current from the second winding 6.

The junction between the second winding 6 and the measurement resistance 7 is connected to the inverting input of a difference amplifier 11 the non-inverting input of which is acted on by a bias voltage which is obtained from the operating voltage by means of a voltage divider comprising resistors 12, 13. The output of the difference amplifier 11 is connected to an input 14 of a microcomputer 15 which, via an output 16, controls the switching transistor 8.

Figure 2:
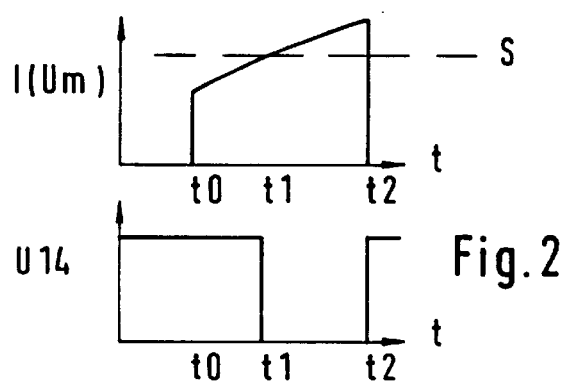
FIG. 2 is a time graph of the current through the second winding.

FIG. 2 shows, in the from of a time graph, the current I through the measurement resistor 7 and the voltage drop Um over the measurement resistor 7, as well as the output voltage U14 of the difference amplifier 11. At the time t0, the switching transistor 8 is switched into the conductive state. The voltage applied by said switching to the second winding 6 of the isolating transformer 9 acts on an impedance having an ohmic component and an inductive component, the ohmic component being dependent on the value of the resistance of the wetness sensor 1. Therefore, at t0, the current first rises rapidly and then continues to rise gradually until it exceeds a threshold value S. The time when it exceeds said value is dependent on the resistance of the wetness sensor 1 and can be determined in the manner that the period of time between t0 and t1 is measured by a counting process in the microcomputer 15. At the time t2, the switching transistor 8 is then again brought into the non-conductive state, whereupon the current through the second winding 6 and the measurement resistor 7 drops relatively rapidly over the diode 10.

Figure 3:
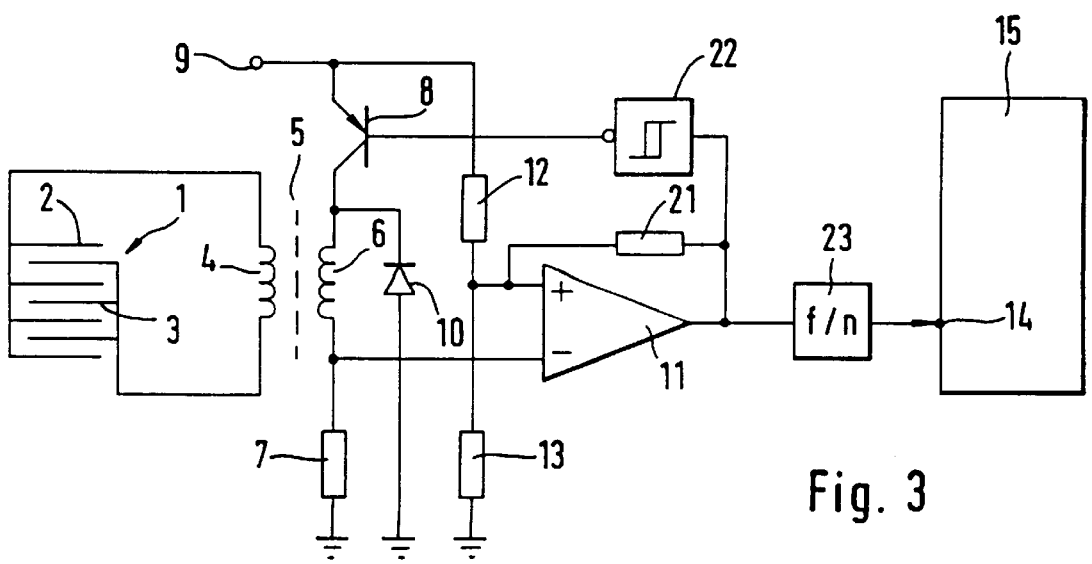
FIG. 3 shows a second embodiment.

In the embodiment shown in FIG. 3, the output of the difference amplifier 11 is fed back via a resistor 21 to the non-inverting input. Furthermore, the switching transistor 8 is controlled by the output voltage of the difference amplifier 11 via an inverter 22. Thus, the circuit oscillates at a frequency which is dependent on the value of the resistance of the wetness sensor 1, which can be measured by the microcomputer 15. This can take place, for instance, in the manner that, for a predetermined period of time, the number of flanks of the output signal of the difference amplifier 11 are counted. Should the frequency, however, be too high with respect to the microcomputer 15 itself or with respect to the functioning of other programs in the microcomputer, a frequency divider 23 can be provided between the output of the difference amplifier 11 and the input 14 of the microcomputer 15.

Figure 4:
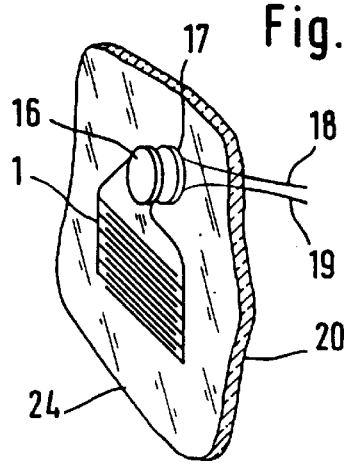
FIG. 4 shows a locating of transformer windings on opposite sides of a window.

In the embodiment shown in FIG. 4, the isolating transformer is not developed in one piece. Rather, the primary winding 16 and the secondary winding 17, including the core material possibly present are divided between the inner side 20 of the window of the vehicle and the outer side 21 thereof. The transfer of energy to the resistance sensor 1 thus takes place inductively. There are no wire lead-throughs between the inner side and the outer side of the window of the vehicle. The secondary winding 17 is connected to the evaluation circuit via wires 18, 19.

I claims:

1. A sensor circuit for measuring the resistance of a resistance sensor located on a a first surface of a window of a vehicle, comprising:

an evaluation circuit located on a second surface of the window opposite the first surface, the sensor being connected to the evaluation circuit;

wherein a galvanic separation is present between the resistance sensor and the evaluation circuit;

for obtaining the galvanic separation, the sensor circuit further comprises a transformer having a first transformer winding disposed on said first surface and connecting with said sensor, and a second transformer winding disposed on said second surfaces and connecting with said evaluation circuit, resistance of said sensor being reflected by said transformer as a resistive component of impedance appearing in circuit with said second winding;

said evaluation circuit further comprises a resistive element in series with said second winding, and means for applying a pulse-like voltage across a series combination of said resistance element and said second winding resulting in a flow of current through said second winding beginning with an initial value and increasing from said initial value to attain a threshold value of current, the moment of attainment the threshold being dependent on the resistance of said sensor and said resistance element; and said evaluation circuit includes means for measuring time elapsed from a beginning of said pulse-like voltage and the moment of attainment of the threshold current, the elapsed time being a measure of the resistance of the sensor.

2. A sensor according to claim 1, wherein said sensor is a rain sensor, and said window is disposed in a vehicle with said first surface being receptive to rain, said transformer connection inhibiting electrolytic degradation of electrodes of said rain sensor.

3. A sensor circuit for measuring fluid on a windshield, comprising:

a first circuit part and a second circuit part;

wherein said first circuit part includes a sensor, and said second circuit part includes an evaluation circuit for measuring resistance of the sensor;

said first circuit part is located on a first side of the windshield; and connection of said first circuit part to said second circuit part is made through the windshield by inductive coupling, thereby attaining a galvanic separation between said sensor and said evolution circuit;

said inductive coupling comprises a transformer having a first transformer winding disposed on said first surface and connecting with said sensor, and a second transformer winding sisposed on said second surface and connecting with said evaluation circuit, resistance of said sensor being reflected by said transformer as a resistive component of impedance appearing in circuit with said second winding;

said evaluation circuit further comprises a resistive element in series with said second winding, and means for applying a pulse-like voltage across a series combination of said resistance element and said second winding resulting in a flow of current through said second winding beginning with an initial value and increasing from said initial value to attain a threshold value of current greater then said initial value of current, the moment of attaining the threshold being dependent on the resistance of said sensor and said resistance element; and said evaluation circuit includes means for measuring time elapsed from a beginning of said pulse-like voltage and the moment of attainment of the threshold current, the elapsed time being a measure of the resistance of the sensor.

4. A sensor circuit for measuring the resistance of a resistance sensor located on a first surface of a electrically non-conductive substrate, the sensor circuit comprising:

an evaluation circuit having components located on a second surface of said substrate opposite said first surface, said evaluation circuit serving to measure said resistance; and means for coupling said components of said evaluation circuit through said substrate to said sensor while maintaining a galvanic separation between said sensor and said evaluation circuit;

wherein said coupling means operates inductively;

said sensor has resistance depending on a presence of electrically conductive material on said first surface;

said coupling means comprises a transformer having a first transformer winding disposed on said first surface and connecting with said sensor, and a second transformer winding disposed on said second surface and connecting with said evaluation circuit, resistance of said sensor being reflected by said transformer as a resistive component of impedance appearing in circuit with said second winding;

said evaluation circuit further comprises a resistive element in series with said second winding, and means for applying a pulse-like voltage across a series combination of said resistance element and said second winding resulting in a flow of current through said second winding beginning with an initial value and increasing from said initial value to attain a threshold value of current greater than said initial value of current, the moment of attaining the threshold being dependent on the resistances of said sensor and said resistance element.

5. A sensor circuit for measuring the resistance of a resistance sensor, comprising:

an isolation transformer;

an evaluation circuit, the sensor being connected to the evaluation circuit;

wherein a galvanic separation is present between the resistance sensor and the evaluation circuit;

the galvanic separation is formed by the isolation transformer;

the isolation transformer comprises a first winding and a second winding;

the evaluation circuit further comprises a resistive element in series with the second winding, means for providing a pulse-like voltage to a series combination of the resistance element and the second winding, and means coupled to the second winding for measuring a time period;

the resistance sensor is connected to the first winding of the isolation transformer, resistance of the sensor being reflected by the transformer as a resistive component of impedance appearing in circuit with the second winding;

the second winding of the isolation transformer is energized by the pulse-like voltage;

during each pulse of the pulse-like voltage, a current through the second winding increases from a minimum value of current present at the beginning of the pulse-like voltage; and the measuring means is operative to measure a period of time extending from a start of the pulse to a point in time wherein the current in the second winding reaches a predetermined threshold greater than the minimum value of current, the moment of attaining the threshold being dependent on the resistances of the moisture sensor and the resistance element;

wherein the second winding presents to the voltage-providing means an impedance with an ohmic and an inductive component, with the ohmic component depending on the magnitude of the resistance of the sensor, the length of the period of time serving as a measure of the resistance of the sensor.

6. A sensor circuit comprising a sensor and an evaluation circuit and means for coupling the sensor to the evaluation circuit for measuring an electrical parameter of the sensor;

wherein said sensor is disposed on a first surface of a non-conductive substrate, said sensor having a first set of electrodes and a second set of electrodes interleaved with electrodes of said first set of electrodes, the electrodes of said first sheet being spaced apart from the electrodes of said second set to enable said electrical parameter of said sensor to be dependent on an electrical parameter of a liquid located on said first surface;

components of said evaluation circuit are disposed on a second surface of said substrate, said coupling means being operative to communicate electromagnetically through said substrate for coupling said sensor to said components of said evaluation circuit; and said evaluation circuit measures said electrical parameter of said sensor to determine an amount of the liquid on said first surface;

wherein said coupling means comprises a transformer having a first transformer winding disposed on said first surface and connecting with said sensor, and a second transformer winding disposed on said second surface and connecting with said evaluation circuit, resistance of said sensor being reflected by said transformer as a resistive component of impedance appearing in circuit with said second winding;

said evaluation circuit further comprises a resistive element in series with said second winding, and means for applying a pulse-like voltage across a series combination of said resistance element and said second winding resulting in a flow of current through said second winding beginning with an initial value and increasing from said initial value to attain a threshold value of current greater than said initial value of current, the moment of attaining the threshold being dependent on the resistances of said sensor and said resistance element; and said components of said evaluation circuit including means for measuring time elapsed from a beginning of said pulse-like voltage and the moment of attainment of the threshold current, the elapsed time being a measure of the resistance of the sensor.

7. A sensor circuit comprising a sensor and an evaluation circuit and means for coupling the sensor to the evaluation circuit for measuring and electrical parameter of the sensor;

wherein said sensor is disposed on a first surface of a non-conductive substrate, said sensor having a first set of electrodes and a second set of electrodes interleaved with electrodes of said first set of electrodes, the electrodes of said first set being spaced apart from the electrodes of said second set to enable said electrical parameter of said sensor to be dependent on an electrical parameter of a liquid located on said first surface;

components of said evaluation circuit are disposed on a second surface of said substrate, said coupling means being operative to communicate electromagnetically through said substrate for coupling said sensor to said components of said evaluation circuit;

said evaluation circuit measures said electrical parameter of said sensor to determine an amount of the liquid on said first surface, said electrical parameter including resistance;

said coupling means comprises a transformer having a first transformer winding disposed on said first surface and connecting with said sensor, and a second transformer winding disposed on said second surface and connecting with evaluation circuit, resistance of the sensor being reflected by the transformer as a resistive component of impedance appearing in circuit with the second winding;

said first and said second windings of said transformer are inductively coupled, and only said second winding is connected via electrical conductors to said evaluation circuit;

wherein said evaluation circuit comprises:
- a resistive element in series with the second winding, means for applying an electrical pulse to a series combination of the resistance element and said second winding, and means for providing a measurement of current in said second winding, said winding current changing in time from a minimum value of the current present at the beginning of the electrical pulse in dependency on an amount of said parameter;
- means for measuring time elapsed from a beginning of the electrical pulse until said current measurement attains a predetermined threshold current value, the threshold value being greater than the minimum value of current; and
- means for responding to said current upon said current attaining the predetermined value, the elapsed time being a measure of the electrical Parameter of the sensor.

8. A sensor circuit according to claim 5, wherein the resistor is connected to a first terminal of the secondary winding, the sensor circuit further comprises a source of operating voltage, the evaluation circuit further comprises a switching transistor coupled to a second terminal of the secondary winding, the measuring means further comprises a difference amplifier and a source of predetermined potential;

the secondary winding is connected, in series with the measurement resistor, to one pole of the source of operating voltage and, via the switching transistor, to a second pole of the source of operating voltage; and a junction of the second winding with the measurement resistor is connected to one input of the difference amplifier, a second input of the difference amplifier being connected to the source of predetermined potential.

9. A sensor circuit according to claim 8, wherein the resistance is a first resistor of the measuring means, and the measuring means further comprises a second resistor, an inverter, and a microprocessor;

an output of the difference amplifier is connected, via the second resistor, to a non-inverting input of the difference amplifier and, via the inverter, to a control input of the switching transistor; and the output of the difference amplifier is connected to an input of the microcomputer.

10. A sensor circuit according to claim 9, further comprising a frequency divider, wherein the input of the microcomputer is connected, via the frequency divider, to the output of the difference amplifier.

11. A sensor circuit according to claim 8, wherein the measuring means comprises a microcomputer;

the switching transistor is controlled by the microcomputer; and an output of the difference amplifier is connected to an input of the microcomputer.

12. A sensor circuit according to claim 8, further comprising a diode, wherein the diode is connected in parallel to a series arrangement of the second winding and the measurement resistor.

13. A sensor according to claim 4, wherein said conductive material is a liquid, and said substrate is a window.

14. A sensor circuit according to claim 7, wherein said responding means includes means for cleaning said substrate, and means responsive to said current measurement for activating said cleaning means.

15. A sensor circuit according to claim 14, wherein said substrate is a window, and said cleaning means is a wiper.

16. A sensor according to claim 15, wherein said parameter is resistance, and said winding current increases in time dependency on an amount of said resistance.

17. A sensor according to claim 4, wherein said evaluation circuit comprises a feedback circuit producing an oscillatory signal, said sensor serving as a part of said feedback circuit, the resistance of said sensor controlling a value of a frequency of said oscillatory signal.

* * * * *